United States Patent
Nakano (10) Patent No.: US 9,295,371 B2
(45) Date of Patent: Mar. 29, 2016

(54) MEASURING ENDOSCOPE APPARATUS AND PROGRAM

(71) Applicant: Olympus Corporation, Tokyo (JP)

(72) Inventor: Sumito Nakano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 443 days.

(21) Appl. No.: 13/661,350

(22) Filed: Oct. 26, 2012

(65) Prior Publication Data
US 2014/0028819 A1 Jan. 30, 2014

(30) Foreign Application Priority Data

Jul. 25, 2012 (JP) ................................. 2012-165028

(51) Int. Cl.
| | | |
|---|---|---|
| H04N 7/18 | (2006.01) | |
| A62B 1/04 | (2006.01) | |
| A61B 1/00 | (2006.01) | |
| G02B 23/24 | (2006.01) | |
| G02B 23/26 | (2006.01) | |
| G01D 11/00 | (2006.01) | |

(52) U.S. Cl.
CPC ......... *A61B 1/00009* (2013.01); *A61B 1/00057* (2013.01)

(58) Field of Classification Search
CPC ............ A61B 1/00; A61B 1/04; G02B 23/24; G02B 23/26; G01D 11/00
USPC ............................... 348/65; 324/326; 345/735
See application file for complete search history.

(56) References Cited

U.S. PATENT DOCUMENTS

| | | | | |
|---|---|---|---|---|
| 5,460,029 A | * | 10/1995 | Tuot ............................... 73/1.34 |
| 2003/0095141 A1 | * | 5/2003 | Shah et al. .................... 345/735 |
| 2010/0060285 A1 | * | 3/2010 | Pearson et al. ................ 324/326 |

FOREIGN PATENT DOCUMENTS

| | | | | |
|---|---|---|---|---|
| JP | 2001004412 A | * | 1/2001 | ............ G01D 11/00 |
| JP | 2004-049638 A | | 2/2004 | |
| JP | 2004-275359 A | | 10/2004 | |
| JP | 2011-169677 A | | 9/2011 | |

* cited by examiner

*Primary Examiner* — Sath V Perungavoor
*Assistant Examiner* — Patricia I Young
(74) *Attorney, Agent, or Firm* — Holtz, Holtz & Volek PC (57) ABSTRACT

An imaging section images a subject to generate an image. A display displays an image. A measuring section measures the size of the subject on the basis of the image. A recording section associates calibration data of a measuring endoscope apparatus including a value obtained when the measuring section measures the size of the calibrator on the basis of an image obtained when the imaging section has imaged the calibrator, and calibration data of the calibrator including a value obtained when the calibrator is measured by a higher-rank measuring instrument of a traceability system, and a value obtained when the measuring section measures the size of a measurement object different from the calibrator on the basis of an image of the measurement object, with the image of the measurement object image and records the associated data on a recording medium.

8 Claims, 6 Drawing Sheets

|     | CALIBRATION CERTIFICATE | | |
|---|---|---|---|
|     |                 | SCOPE | OPTICAL ADAPTER |
| 600 | PRODUCT NAME    |       |         |
|     | MODEL NAME      |       |         |
|     | MANUFACTURING NUMBER |  |         |
|     | MANUFACTURER    | OLYMPUS CORPORATION | |
|     | EXAMINATION REPORT NUMBER | | |
| 601 | CALIBRATION DATE | . . | |

IT IS CERTIFIED THAT THE ABOVE PRODUCT HAS BEEN CALIBRATED BASED ON A CALIBRATION SYSTEM BASED ON A STANDARD INSTRUMENT GROUP THAT HAS TRACED NATIONAL STANDARDS OR INTERNATIONAL STANDARDS.

DEPARTMENT : ___________________

SIGNED BY : ___________________

FIG. 7

EXAMINATION REPORT

|  | SCOPE | OPTICAL ADAPTER |
|---|---|---|
| 700 — PRODUCT NAME | _______ | _______ |
| MODEL NAME | _______ | _______ |
| MANUFACTURING NUMBER | _______ | _______ |
| EXAMINATION REPORT NUMBER | _______ | |
| 701 — EXAMINATION EXECUTION DATE | __.__.__ | |
| 702 — EXAMINATION RESULTS | _______ | |
| TEMPERATURE | _______ °C | |
| STANDARD INSTRUMENT | _______ | |
| MANUFACTURER | OLYMPUS CORPORATION | |
| 703 — NEXT CALIBRATION DATE | __.__.__ | |

DEPARTMENT : _______________

SIGNED BY : _______________

MEASURING ENDOSCOPE APPARATUS AND PROGRAM

BACKGROUND OF THE INVENTION

1. Field of the Invention

The present invention relates to a measuring endoscope apparatus having a measuring function, and a program for making a computer function as the measuring endoscope apparatus.

Priority is claimed on Japanese Patent Application No. 2012-165028, filed Jul. 25, 2012, the contents of which are incorporated herein by reference.

2. Description of the Related Art

In recent years, in the examination of boilers, turbines, engines, chemical processing plants, or the like, industrial endoscopes are widely used for observing the damage or corrosion of the interior. As shown in Japanese Unexamined Patent Application, First Publication No. 2004-49638, a measuring endoscope apparatus in which two optical systems are provided at the tip of an endoscope is proposed as an example of the industrial endoscopes. In this measuring endoscope apparatus, images of a subject are taken from two different positions, and three-dimensional measurement is realized by stereo measurement utilizing the principle of triangulation. The necessity for disassembling and repairing can be determined by measuring the size or the like of the damage using such a measuring endoscope apparatus when defective parts, such as damaged parts, are discovered inside an examined object in the examination.

It is necessary to periodically perform calibration of measuring instruments, such as this measuring endoscope apparatus, using an object (hereinafter referred to as calibrator) with known length like a standard scale. The calibrator is measured by a higher-rank measuring instrument in a traceability system. This ensures the reliability of the values of the calibrator. A calibrator for the measuring endoscope apparatus is described in Japanese Unexamined Patent Application, First Publication No. 2004-275359. The calibration of a measuring instrument, such as the measuring endoscope apparatus, is performed by comparing a value obtained when the measuring instrument measures a calibrator with a value obtained when a higher-rank measuring instrument in a traceability system measures the calibrator, and obtaining a measurement error. By performing the calibration of the measuring instrument, such as the measuring endoscope apparatus, using this calibrator, the relationship between the value obtained when the measuring instrument measures, and the value of the calibrator as a standard is established, and the reliability of measurement results obtained by performing measurement of a subject using the measuring instrument is ensured.

Figure 6:
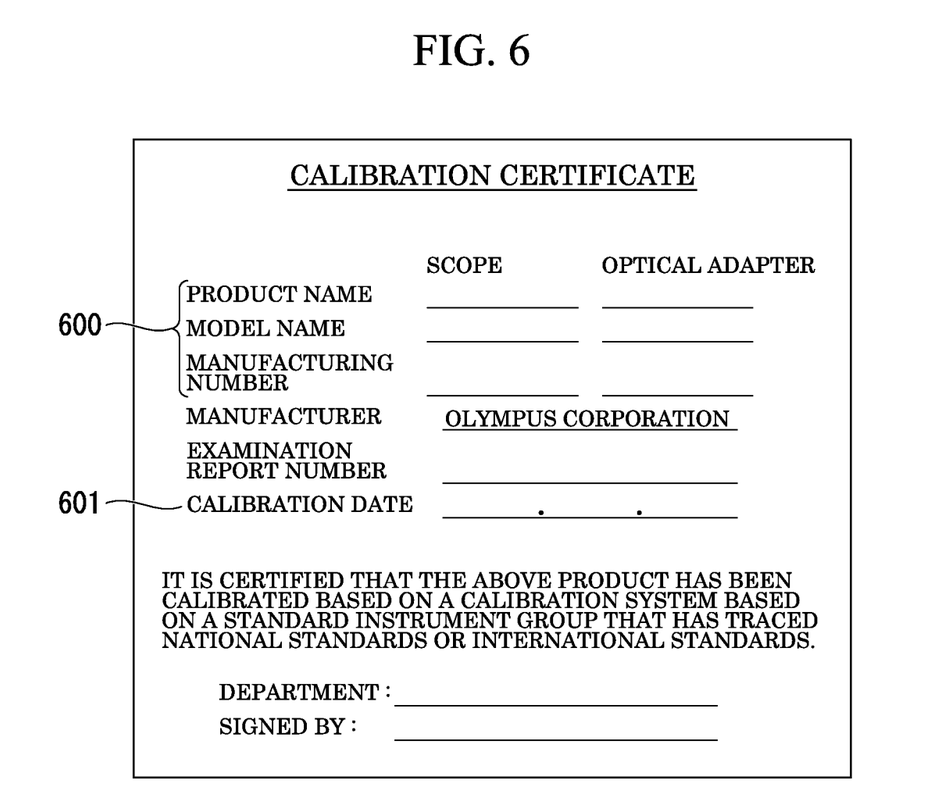
FIG. 6 is a reference view showing the contents of a calibration certificate.

The results obtained when the measuring instrument, such as the measuring endoscope apparatus, is calibrated are written, for example, in a calibration certificate. Presentation of the calibration certificate may be required if necessary. FIG. 6 shows an example of the calibration certificate. Information 600 on the measuring instrument, such as the measuring endoscope apparatus that measures the calibrator, a calibration date 601 that is the date when calibration of the measuring instrument, such as the measuring endoscope apparatus is measured, and the like are written in the calibration certificate.

Figure 7:
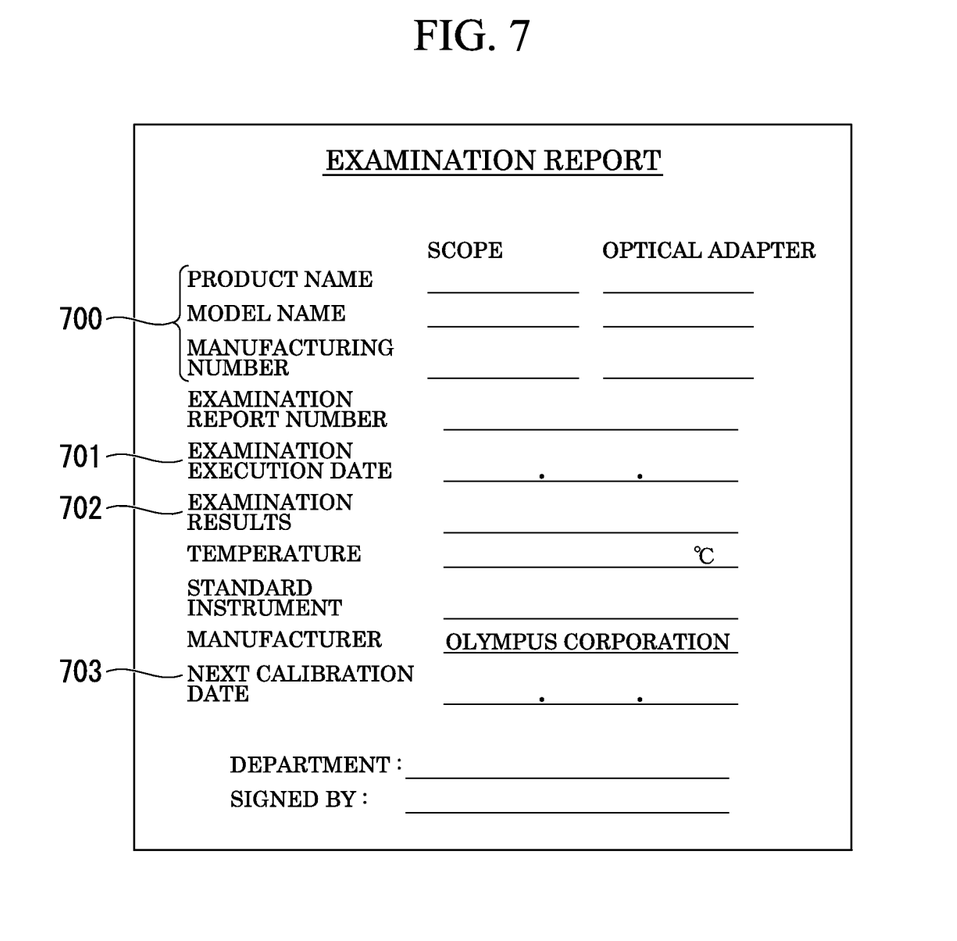
FIG. 7 is a reference view showing the contents of an examination report.

Additionally, the results obtained when a subject is measured using the measuring instrument, such as the measuring endoscope apparatus, are written, for example in an examination report. FIG. 7 shows an example of the examination report. Information 700 on a measuring instrument, such as the measuring endoscope apparatus that measures a subject, an examination execution date 701 that is the date when measurement of the subject is measured, measurement results 702 that are measurement results of the subject, a calibrator (standard instrument) 703 used for the calibration of the measuring instrument such as the measuring endoscope apparatus, and the like are written in the examination report.

A method of more simply performing the calibration of a measuring instrument is described in Japanese Unexamined Patent Application, First Publication No. 2011-169677. In Japanese Unexamined Patent Application, First Publication No. 2011-169677, a two-dimensional code including calibration data of a calibrator that is the results obtained when a higher-rank measuring instrument in a traceability system that measures the calibrator is pasted on the calibrator. The calibration data of the calibrator is incorporated into the measuring instrument by reading the two-dimensional code during calibration of the measuring instrument. Thereafter, a measurement error is obtained by comparing a value obtained when the measuring instrument measures the calibrator with the value of the calibration data of the calibrator. Since this can save time and effort for inputting the calibration data of the calibrator to the measuring instrument, the measuring instrument can be more simply calibrated.

In order to ensure the reliability of measurement results, it is necessary to ensure the traceability of the measuring instrument, such as the measuring endoscope apparatus, and the traceability of the measurement results. By leaving the fact that calibration of the measuring instrument, such as the measuring endoscope apparatus, is performed, as a record, the traceability of the measuring instrument, such as the measuring endoscope apparatus, is ensured. Additionally, the traceability of the measurement results is ensured by associating the record that calibration of the measuring instrument, such as the measuring endoscope apparatus, is performed, and the results obtained when a subject is measured by the measuring instrument, such as the measuring endoscope apparatus.

SUMMARY OF THE INVENTION

A measuring endoscope apparatus related to a first aspect of the present invention includes an imaging section that images a subject to generate an image; a display that displays the image; a measuring section that measures the dimensions of the subject based on the image; an input section that inputs a first calibration data of a calibrator used when the measuring endoscope apparatus is adjusted; and a recording section that associates a second calibration data of the measuring endoscope apparatus including a first value obtained when the measuring section measures the calibrator based on a calibrator image obtained when the imaging section images the calibrator, and the first calibration data and a second value obtained when the measuring section measures a measurement object based on an object image of the measurement object that is different from the calibrator, with the object image and records an associated data on a recording medium.

According to a second aspect of the present invention, the measuring endoscope apparatus related to the first aspect further may include a generator that reads the second calibration data from the recording medium, and generates a calibration certificate of the measuring endoscope apparatus.

According to a third aspect of the present invention, in the measuring endoscope apparatus related to the first aspect or the second aspect, the second calibration data may include a calibration expiry date.

According to a fourth aspect of the present invention, in the measuring endoscope apparatus related to the third aspect, the display section may display a message that calls attention to when the remaining days until the calibration expiry date are less than the predetermined number of days or when the remaining days have passed the calibration expiry date.

According to a fifth aspect of the present invention, the measuring endoscope apparatus related to any one of the first to fourth aspects may further include a report generator that reads the second calibration data from the recording medium and generates an examination report according to a predetermined format, based on the second value obtained when the measuring section measures the measurement object, the object image, and the second calibration data.

According to a sixth aspect of the present invention, in the measuring endoscope apparatus related to any one of the first to fifth aspects, the input section may input the first calibration data including a third value obtained when the calibrator is measured by a higher-rank measuring instrument of a traceability system.

According to a seventh aspect of the present invention, in the measuring endoscope apparatus related to the sixth aspect, the first calibration data may include at least one of a type of the calibrator, an identification information of the calibrator, a calibration results of the calibrator, and an apparatus information of the higher-order measuring instrument of the traceability system.

According to an eighth aspect of the present invention, in the measuring endoscope apparatus related to any one of the first to seventh aspects, the calibrator may have a reference showing the dimensions, and a coded first calibration data.

According to a ninth aspect of the present invention, in the measuring endoscope apparatus related to the eighth aspect, the input section may input the first calibration data by decoding the coded first calibration data based on the calibrator image.

According to a tenth aspect of the present invention, in the measuring endoscope apparatus related to the eighth aspect or the ninth aspect, the measuring section may calculate a fourth value obtained when the size of the reference of the calibrator is measured, based on the calibrator image.

According to an eleventh aspect of the present invention, in the measuring endoscope apparatus related to any one of the sixth to tenth aspects, the measuring section may change parameters to be used for measurement, when the error between the third value obtained when the calibrator is measured by the higher-order measuring instrument of the traceability system and the first value obtained when the measuring section measures the calibrator is larger than a predetermined value.

A program related to a twelfth aspect of the present invention has a computer of a measuring endoscope apparatus including an imaging section that images a subject to generate an image; a display that displays the image; and a measuring section that measures the dimensions of the subject based on the image, the computer including an input section that inputs a first calibration data of a calibrator used when the measuring endoscope apparatus is adjusted; and a recording section that associates a second calibration data of the measuring endoscope apparatus including a first value obtained when the measuring section measures the calibrator based on a calibrator image obtained when the imaging section images the calibrator, and the first calibration data, and a second value obtained when the measuring section measures a measurement object based on an object image of the measurement object that is different from the calibrator, with the object image and records the associated data on a recording medium.

DETAILED DESCRIPTION OF THE INVENTION

Figure 1:
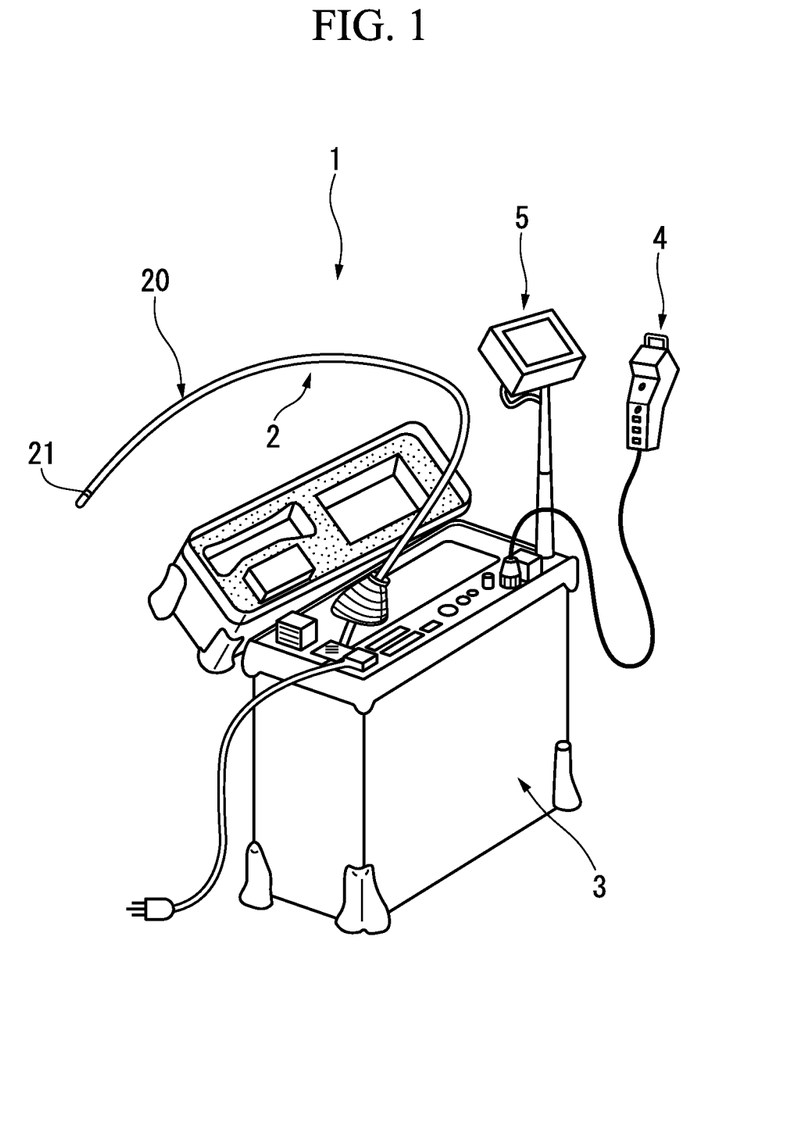
FIG. 1 is a perspective view showing the overall configuration of a measuring endoscope apparatus according to one embodiment of the present invention.

Embodiments of the present invention will be described below with reference to the drawings. FIG. 1 shows the overall configuration of a measuring endoscope apparatus according to one embodiment of the present invention. As shown in FIG. 1, the measuring endoscope apparatus 1 includes an endoscope 2 that has an elongated insertion part 20, a control unit 3 that is a control device including a housing portion that houses the insertion part 20 of the endoscope 2, an operating part 4 for performing the operation required when a user performs various operation controls of the overall apparatus, and a display 5 that displays an endoscope image, the contents of the operation control (for example, processing menu), or the like. A tip portion 21 is arranged at the tip of the insertion part 20. An optical adapter having an optical system for taking the light from a subject that is a measurement object (examination object) into the tip portion 21 can be mounted on the tip portion 21. For example, two subject images corresponding to different viewpoints can be formed by mounting a stereo optical adapter on the tip portion 21 during measurement.

Figure 2:
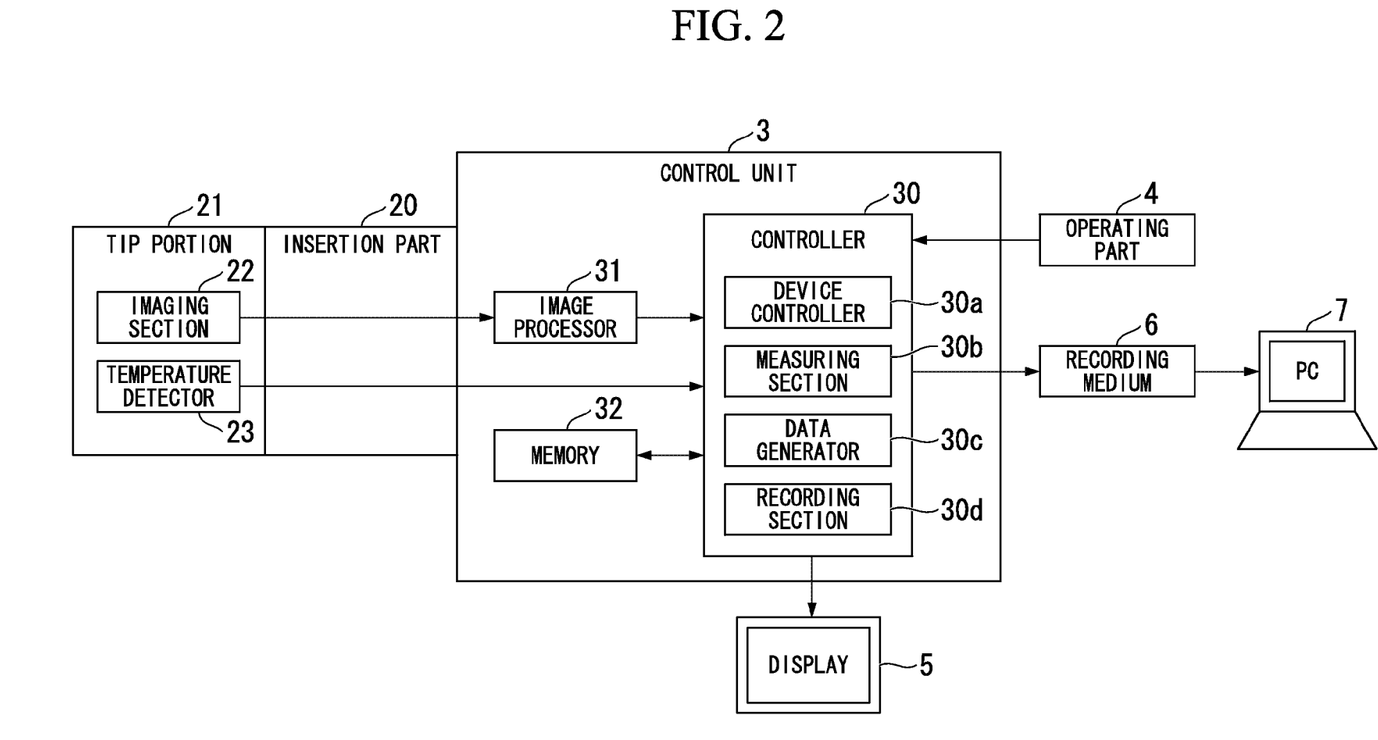
FIG. 2 is a block diagram showing the configuration of the measuring endoscope apparatus according to one embodiment of the present invention.

FIG. 2 shows the internal configuration of the measuring endoscope apparatus 1. The measuring endoscope apparatus 1 includes an imaging section 22 that images a subject to generate an image, a display 5 that displays the image, a measuring section 30b that measures the dimensions of the subject on the basis of the image, an input section that inputs a first calibration data of a calibrator 400 used when the measuring endoscope apparatus 1 is adjusted, and a recording section 32 that associates a second calibration data of the measuring endoscope apparatus 1 including a value (first value) obtained when the measuring section 30b measures the calibrator 400 on the basis of an image obtained when the imaging section 22 has imaged the calibrator 400, and the first calibration data of the calibrator 400, and a value (second value) obtained when the measuring section 30b measures a measurement object different from the calibrator 400 on the basis of an object image of the measurement object, with the object image of the measurement object and records the associated data on a recording medium. The respective members will be described below in detail.

The tip portion 21 arranged at the tip of the insertion part 20 has the imaging section 22 and a temperature detector 23. The imaging section 22 has an imaging element that images a subject to generate image data. The temperature detector 23 has a thermistor that detects a surrounding temperature.

The control unit 3 has a controller 30, an image processor 31, and a memory 32. The controller 30 reads a control program stored in the memory 32 and executes commands described in the control program, thereby performing various kinds of control. The controller 30 has a device controller 30a, a measuring section 30b, a data generator 30c, and a recording section 30d.

The device controller 30a controls respective sections within the measuring endoscope apparatus 1. The measuring section 30b measures the dimensions of a subject on the basis of the image data output from the imaging section 22. The data generator 30c generates the calibration data (second calibration data) of the measuring endoscope apparatus 1, an image file to be described below, and the like. The recording section 30d records data, such as the image file, on a storage medium 6 that is a recording medium that can be attached to and detached from the measuring endoscope apparatus 1.

The image processor 31 performs various kinds of image processing on the image data output from the imaging section 22. The memory 32 has a nonvolatile memory that stores calibration data (first calibration data) of the calibrator, calibration data of the measuring endoscope apparatus 1, a control program for operating the controller 30, and the like. The image file recorded on the storage medium 6 can be viewed by a PC (personal computer) 7.

The control program of the measuring endoscope apparatus 1 may be recorded on a computer readable recording medium, and computers other than measuring endoscope apparatus 1 may be made to read and execute the control program recorded on this recording medium. For example, the PC 7 may read and execute the control program, transmit control information for controlling the measuring endoscope apparatus 1 to the measuring endoscope apparatus 1, to control the measuring endoscope apparatus 1, according to the control program, and makes the measuring endoscope apparatus 1 perform measurement.

Here, if the "computer" is a case where the WWW system is used, the computer also includes a homepage-providing environment (or display environment). Additionally, the term "computer-readable recording medium" includes portable media, such as floppy disks, magneto-optical disks, ROMs, CD-ROMs, DVD-ROMs, and flash memory, and memory devices built into the computer. Moreover, the "computer-readable recording medium" includes media holding a program for a given period of time, like a volatile memory (RAM) inside a computer system used as a server or a client when a program is transmitted via networks, such as the Internet, or communication lines, such as telephone lines.

Additionally, the above-described program may be transmitted to other computers from a computer, which stores this program in a memory device or the like, via a transmission medium or by transmission waves in the transmission medium. Here, the "transmission medium" that transmits a program means a medium that has the function to transmit information, like networks (communication networks), such as the Internet, or communication lines (communication wires), such as telephone lines. Additionally, the above-described program realizes some of the aforementioned functions. Moreover, a so-called difference file (difference program) can realize the aforementioned functions in combination with programs already recorded in the computer.

Figure 3:
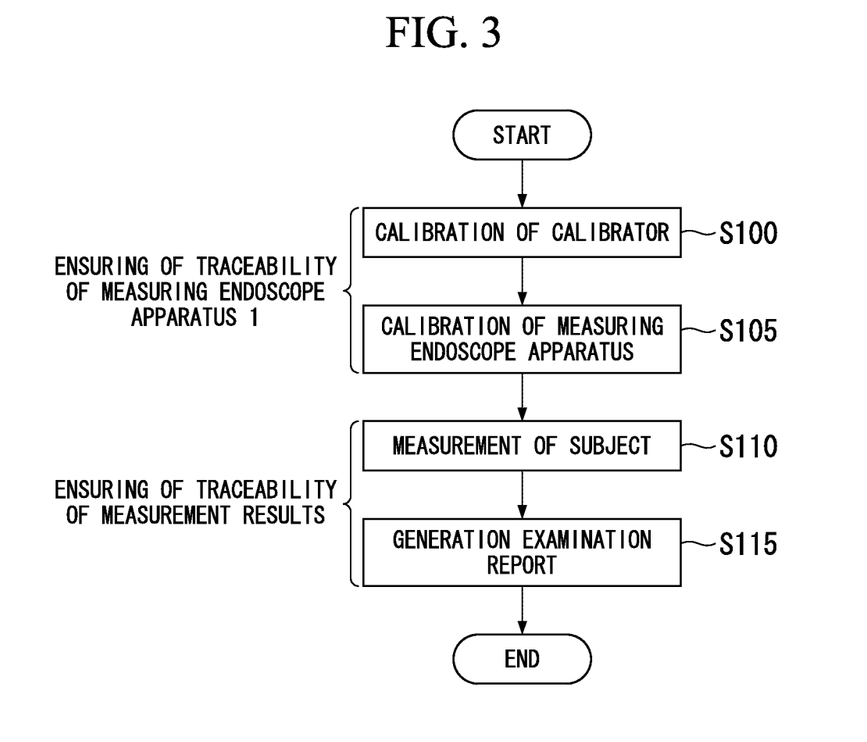
FIG. 3 is a flowchart showing the procedure of ensuring the traceability of the measuring endoscope apparatus according to one embodiment of the present invention and the traceability of measurement results.
Figure 4:
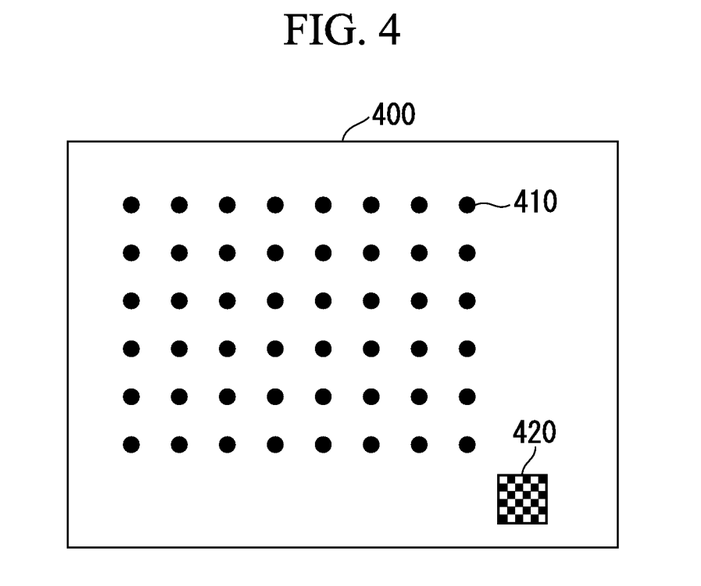
FIG. 4 is a plan view of a calibrator to be used for the calibration of the measuring endoscope apparatus according to one embodiment of the present invention.

Next, a method of ensuring the traceability of the measuring endo scope apparatus 1 and the traceability of the measurement results will be described. FIG. 3 shows the procedure of ensuring the traceability of the measuring endoscope apparatus 1 and the traceability of measurement results. First, calibration of the calibrator is performed (Step S100). FIG. 4 is a plan view of a calibrator used for the calibration of the measuring endoscope apparatus 1. As an example, the calibrator 400 has a plane, and a plurality of dots 410 that are referenced are arranged at predetermined intervals to show the dimensions of a subject, and a two-dimensional code 420 including the calibration data of the calibrator 400 is arranged on the plane.

A user, a manufacturer, or a calibrating person of the measuring endoscope apparatus 1 measures the interval of the dots 410 of the calibrator 400 shown in FIG. 4, using a higher-rank measuring instrument in a traceability system, records the calibration data of the calibrator 400 including the measurement results (third value), on the two-dimensional code 420, and pastes the two-dimensional code 420 on the calibrator 400. The calibration data of the calibrator 400 included in the two-dimensional code 420 includes, for example, at least any one among the type of the calibrator 400, the serial number of the calibrator 400, the calibration results of the calibrator 400, and apparatus information on the higher-rank measuring instrument in the traceability system that measures the calibrator 400. The calibration results of the calibrator 400 include, for example, measurement values, temperature, a calibration date, a calibration expiry date, and a worker ID.

The calibration of the measuring endoscope apparatus 1 is performed after the calibration of the calibrator 400 is performed (Step S105). If the user takes a photograph of the calibrator 400 in predetermined conditions using the measuring endoscope apparatus 1, the controller 30 starts calibration of the measuring endoscope apparatus 1. This can start the calibration simply and easily. The calibration of the measuring endoscope apparatus 1 is performed according to the following procedure. The imaging section 22 images the calibrator 400 so as to include the pattern of the dots 410 and the two-dimensional code 420, and generates image data of the calibrator 400. The image processor 31 performs image processing on the image data of the calibrator 400. Thereby, the image processor 31 detects the dots 410. The measuring section 30b calculates the distance between the dots 410 on the basis of the positions of the dots 410 on an image, and generates measurement values (fourth value).

Subsequently, the image processor 31 performs image processing on the image data of the calibrator 400. Thereby, the image processor 31 detects the two-dimensional code 420, and decodes the calibration data of the calibrator 400 from the two-dimensional code 420. The data generator 30c acquires temperature information from the temperature detector 23, and acquires the calibration data of the calibrator 400 from the image processor 31 to generate the calibration data of the measuring endoscope apparatus 1. The data generator 30c stores the generated calibration data of the measuring endoscope apparatus 1 in the memory 32. The calibration data of the measuring endoscope apparatus 1 includes, for example, the apparatus information on the measuring endoscope apparatus 1, the calibration data of the calibrator 400, and the calibration results of the measuring endoscope apparatus 1.

The apparatus information on the measuring endoscope apparatus 1 includes, for example, the serial number of the insertion part 20, and the serial number of the stereo optical adapter. The calibration results of the measuring endoscope apparatus 1 include, for example, the measurement values, the temperature, the calibration date, the calibration expiry date, and the worker ID. The apparatus information on the measuring endoscope apparatus 1 and individual kinds of information of the calibration expiry date and the worker ID are input to the measuring endoscope apparatus 1 and stored in the memory 32, by methods, such as the input of individual kinds of information via the operating part 4, input of individual kinds of information from an external recording medium, such as the storage medium 6, and reception of individual kinds of information from an external device, such as the PC 7. These kinds of information are read from the memory 32 by the data generator 30c during the generation of the calibration data of the measuring endoscope apparatus 1.

In a case where the parameters to be used for measurement need to be changed for such reasons as the errors between the measurement values obtained by performing measurement of the calibrator 400 using the measuring endoscope apparatus 1 and the standard values are larger than predetermined values, for example, parameters in optical data are changed. The optical data is data including parameters or the like of the optical properties of the stereo optical adapter to be mounted on the tip of the tip portion 21. Here, the standard values are values that are set on the basis of measurement results obtained when the calibrator 400 is measured using the higher-rank measuring instrument, or are design values of the calibrator 400. The calibration of the measuring endoscope apparatus 1 is performed as described above.

The calibration of the measuring endoscope apparatus 1 is periodically performed. Consequently, the memory 32 is configured so as to be able to store the calibration data of the measuring endoscope apparatus 1 corresponding to a predetermined number of times of calibration. If the user operates the operating part 4 and inputs generation instruction of a calibration certificate, the data generator 30c reads the calibration data of the measuring endoscope apparatus 1 from the memory 32, and generates a calibration certificate including the calibration data of the measuring endoscope apparatus 1. The calibration certificate is, for example, data in pdf format. The recording section 30d records the generated calibration certificate on the storage medium 6. The calibration certificate may be saved in the memory 32.

As described above, since the fact that the calibration of the measuring endoscope apparatus 1 is performed can be left as a record by generating the calibration data of the measuring endoscope apparatus 1, the traceability of the measuring endoscope apparatus 1 can be ensured. Additionally, the calibration certificate can be easily generated by generating the calibration certificate on the measuring endoscope apparatus 1 that has performed calibration.

The imaging section 22 of the present embodiment functions as an input section that images the two-dimensional code 420 of the calibrator 400. Thereby, the imaging section 22 inputs the calibration data of the calibrator 400 to the measuring endoscope apparatus 1. The method of inputting the calibration data of the calibrator 400 to the measuring endoscope apparatus 1 may be other methods. For example, the calibration data of the calibrator 400 may be input by reading the calibration data of the calibrator 400 from the external recording medium, such as the storage medium 6, or the configuration data of the calibrator 400 may be input by receiving the calibration data of the calibrator 400 from the external device, such as the PC 7. Since an interface section to which an external storage medium is connected functions as an input section in a case where the calibration data of the calibrator 400 is read from the external storage medium, the measuring endoscope apparatus 1 is provided with the interface section. Additionally, since a communication section that communicates with an external device functions as an input section in a case where the calibration data of the calibrator 400 is received from the external device, the measuring endoscope apparatus 1 may be provided with the communication section.

In order to reliably perform the next calibration work, the calibration expiry date may be set in the calibration data of the measuring endoscope apparatus when calibration work is performed. Additionally, in a case where the remaining days until the calibration expiry date becomes less than the predetermined days or in a case where the remaining days have passed the calibration expiry date, the device controller 30a may display a message that prompts user's attention to the display 5. This can prompt a user to perform calibration work.

Measurement of a subject is performed after the calibration data of the measuring endoscope apparatus 1 is generated (Step S110). More specifically, the imaging section 22 images the subject, and generates image data of the subject. The image processor 31 performs image processing on the image data of the subject. Thereafter, according to the control of the device controller 30a, the image data of the subject is output to the display 5, and the image of the subject is displayed on the display 5. The user operates the operating part 4 while viewing the image of the subject, and set measuring points in regions, such as the damage discovered during examination. The measuring section 30b acquires the image data of the subject from the image processor 31, calculates three-dimensional coordinates corresponding to the set measuring points, calculates length or area on the basis of the three-dimensional coordinates corresponding to a plurality of measuring points, and generates measurement values.

Figure 5A:
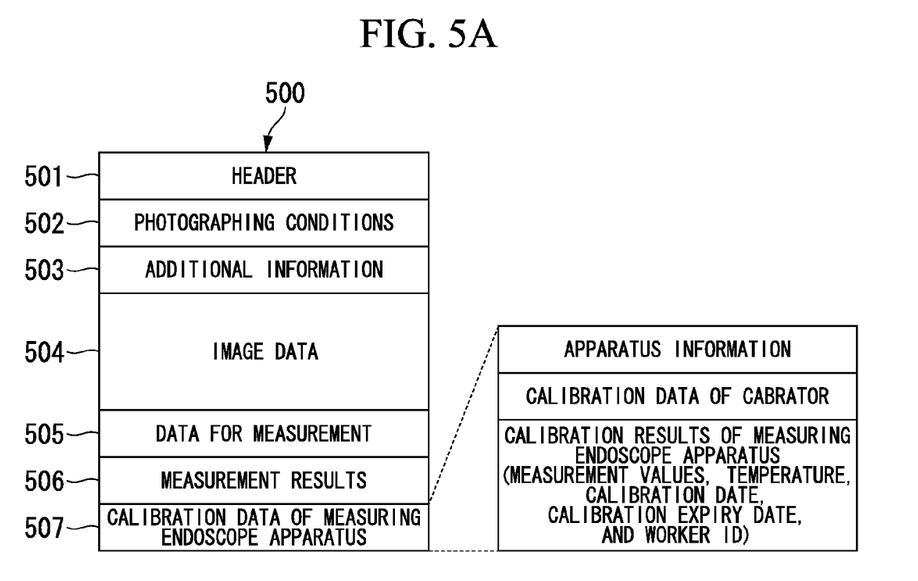
FIG. 5A is a reference view showing the contents of an image file in one embodiment of the present invention.
Figure 5B:
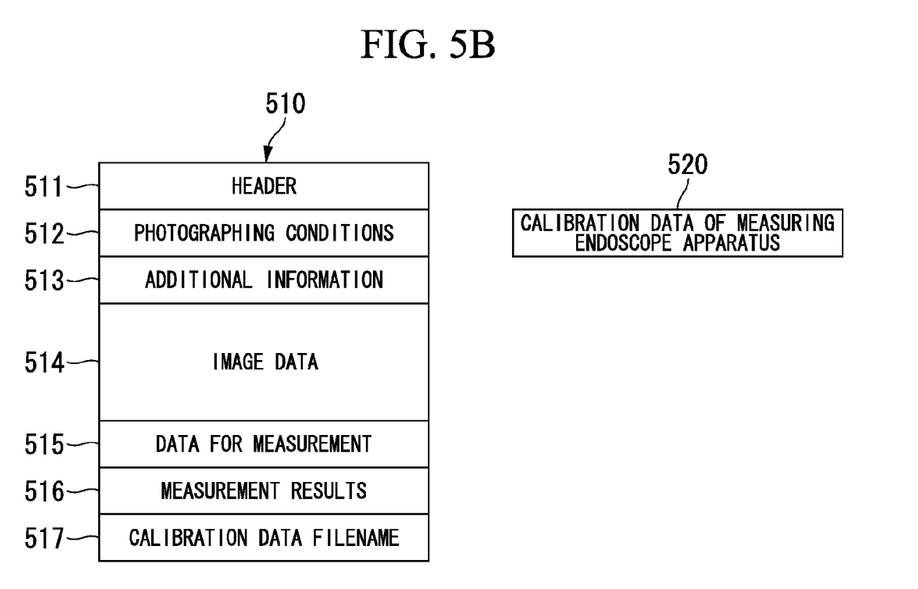
FIG. 5B is a reference view showing the contents of an image file in one embodiment of the present invention.

If the user operates the operating part 4 and inputs an instruction of recording the image on the storage medium 6, the data generator 30c acquires the temperature information from the temperature detector 23, and reads the calibration data of the measuring endoscope apparatus 1 from the memory 32 to generate an image file. FIGS. 5A and 5B show examples of the configuration of image files in the present embodiment. An image file 500 shown in FIG. 5A includes, for example, a header 501, the photographing conditions 502, additional information 503, image data 504, data 505 for measurement, measurement results 506, and calibration data 507 of the measuring endoscope apparatus 1.

The header 501 includes, for example, information showing the configuration of the image file. The photographing conditions 502 include, for example, a photographing date. The additional information 503 includes, for example, characters showing the region of damage, which is input by a user. The image data 504 is image data of a subject acquired from the image processor 31.

The image data 504 may be either still image data or moving image data. The data 505 for measurement includes, for example, parameters and temperature required for measurement. The parameters required for measurement include, for example, optical data including parameters, such as the optical properties of the stereo optical adapter that is a reference, or environmental data obtained by correcting optical data so as to suit the stereo optical adapter used during measurement. The measurement results 506 include, for example, measurement values calculated by the measuring section 30b. The calibration data 507 of the measuring endoscope apparatus 1 is the data read from the memory 32. The recording section 30d records the generated image file 500 on the storage medium 6.

The configuration of the image file may be a configuration shown in FIG. 5B. An image file 510 shown in FIG. 5B includes, for example, a header 511, the photographing conditions 512, additional information 513, image data 514, data 515 for measurement, test results 516, and a filename 517 of calibration data of the measuring endoscope apparatus 1. Portions other than filename 517 of the calibration data of the measuring endoscope apparatus 1 are the same as those of the image file 500 of FIG. 5A. In FIG. 5B, calibration data 520 of the measuring endoscope apparatus 1 is present as a file separate from the image file 510, and the filename thereof is included in the image file 510. The calibration data 520 of the measuring endoscope apparatus 1 is, for example, a file in text data format. The recording section 30d records the generated image file 510 and the calibration data 520 of the measuring endoscope apparatus 1 on the storage medium 6.

As shown in FIG. 5B, the calibration data 520 of the measuring endoscope apparatus 1 does not need to be included in the image file, and may be configured as a separate file correlated with the image file. The calibration data 520 of the measuring endoscope apparatus 1 can be more simply referred to by configuring the calibration data 520 of the measuring endoscope apparatus 1 as a file in a general-purpose format separate from the image file, without using a dedicated application treating the image file.

An examination report is generated after the measurement of the subject is performed (Step S115). More specifically, the user operates the PC 7 to read the image file from the storage medium 6, opens the image file using a dedicated application, and displays the contents of the image file on the screen of the PC 7. At this time, the image, the measurement results, and the calibration data of the measuring endoscope apparatus 1, which are included in the image file, is displayed on the screen of the PC 7. The user operates the PC 7 to copy and paste the image, the measurement results, and the calibration data of the measuring endoscope apparatus 1 on the screen to document data. Thereby an examination report including this data is generated. Similarly, the calibration certificate may be generated on the PC 7. Additionally, the examination report may be generated on the measuring endoscope apparatus 1.

As described above, the traceability of measurement results can be ensured by associating the calibration data of the measuring endoscope apparatus 1 that is a record obtained by performing calibration of the measuring endoscope apparatus 1, measurement results when a subject is measured by the measuring endoscope apparatus 1, and image data used for measurement of the subject. A reliable examination report can be generated by generating the examination report including these data according to a predetermined format. At this time, the device controller 30a functions as a report generator.

Additionally, by associating the image file 500 of FIG. 5A or the image file 510 of FIG. 5B with the calibration data 520 of the measuring endoscope apparatus 1 and saving the associated date, the calibration data is searched from the image file 500 or the image file 510 when the calibration data of the measuring endoscope apparatus 1 is required. Thus, the time and effort for searching the calibration data of the former measuring endoscope apparatus 1 is reduced.

On the examination scene, the image data of a subject is recorded on the storage medium 6 using the measuring endoscope apparatus 1. Thereafter, a method of reading image data into the PC 7 from the storage medium 6 and performing measurements using a dedicated application is also considered. For this reason, for example, the PC 7 may read the above image file from the storage medium 6, perform specifying of the measuring points or calculation of three-dimensional coordinates using the image data in the image file, to obtain measurement results. Thereby, a file for ensuring the traceability of the measurement results and a file for performing measurement can be made common.

As described above, according to the present embodiment, the traceability of measurement results can be ensured while ensuring the traceability of the measuring endoscope apparatus 1 by associating the calibration data of the measuring endoscope apparatus 1, a value obtained by measuring the size of a subject, and the image data of the subject that is used for the measurement, to record the associated data on the storage medium 6.

While a preferred embodiment of the present invention has been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A measuring endoscope apparatus comprising:
an imaging element that images a subject to generate image data; a display;
a memory which stores first calibration data and second calibration data, the first calibration data being calibration data of a calibrator which is used to calibrate the measuring endoscope apparatus, and the second calibration data being calibration data of the measuring endoscope apparatus; and
a controller which is configured to generate measurement data of the subject based on the image data which is obtained by imaging the subject to perform measurement after the first calibration data and the second calibration data have been stored in the memory, and generate an image file to be recorded on a recording medium such that the image file includes the image data, the measurement data, the first calibration data, and the second calibration data,
wherein the controller is configured to read the second calibration data from the memory and generate a calibration certificate of the measuring endoscope apparatus,
wherein the second calibration data includes a calibration expiry date,
wherein the controller is configured to display an alert on the display, when a remaining days until the calibration expiry date are less than a predetermined number days or when the calibration expiry date has passed, and
wherein the controller is configured to read the second calibration data from the recording medium and generate an examination report according to a predetermined format based on the measurement data, the image data, and the second calibration data.

2. The measuring endoscope apparatus according to claim 1, wherein the first calibration data includes a value obtained when the calibrator is measured by a higher-rank measuring instrument of a traceability system.

3. The measuring endoscope apparatus according to claim 2, wherein the first calibration data includes at least one of a type of the calibrator, identification information of the calibrator, a calibration result of the calibrator, and an apparatus information of the higher-rank measuring instrument of the traceability system.

4. The measuring endoscope apparatus according to claim 1, wherein the calibrator has a reference indicating dimensions, and coded first calibration data.

5. The measuring endoscope apparatus according to claim 4, wherein the controller obtains the first calibration data by decoding the coded first calibration data from an image of the calibrator.

6. The measuring endoscope apparatus according to claim 4, wherein the controller is configured to obtain a value by measuring the reference of the calibrator, based on an image of the calibrator.

7. The measuring endoscope apparatus according to claim 2, wherein the controller is configured to change parameters to be used for measurement, when an error between the value obtained when the calibrator is measured by the higher-rank measuring instrument of the traceability system and the value obtained when the controller measures the reference of the calibrator is larger than a predetermined value.

8. A non-transitory computer readable medium storing a program that is executable by a controller of a measuring endoscope apparatus including an imaging element that images a subject to generate image data, a display, and a memory which stores first calibration data and second calibration data, the first calibration data being calibration data of a calibrator which is used to calibrate the measuring endoscope apparatus, and the second calibration data being calibration data of the measuring endoscope apparatus, the second calibration data including a calibration expiry date, the program being executable by the controller to perform functions comprising:

generating measurement data of the subject based on the image data which is obtained by imaging the subject to perform measurement after the first calibration data and the second calibration data have been stored in the memory;

generating an image file to be recorded on a recording medium such that the image file includes the image data, the measurement data, the first calibration data, and the second calibration data;

reading the second calibration data from the memory and generating a calibration certificate of the measuring endoscope apparatus;

displaying an alert on the display, when a remaining days until the calibration expiry date are less than a predetermined number days or when the calibration expiry date has passed; and reading the second calibration data from the recording medium and generating an examination report according to a predetermined format based on the measurement data, the image data, and the second calibration data.

\* \* \* \* \*